United States Patent [19]
Petrillo et al.

[11] 4,219,686
[45] Aug. 26, 1980

[54] PROCESS FOR THE PREPARATION OF ALKYLBENZENES

[75] Inventors: Vincenzo Petrillo; Andrea Peditto, both of Robassomero, Italy

[73] Assignee: Liquichimica Italiana S.p.A., Milan, Italy

[21] Appl. No.: 955,234

[22] Filed: Oct. 27, 1978

Related U.S. Application Data

[63] Continuation of Ser. No. 841,447, Oct. 12, 1977, abandoned, which is a continuation-in-part of Ser. No. 694,228, Jun. 9, 1976, abandoned.

[30] Foreign Application Priority Data

Jun. 11, 1975 [IT] Italy ............................ 24264 A/75

[51] Int. Cl.$^2$ ............................................. C07C 3/56
[52] U.S. Cl. .................................... 585/24; 585/319; 585/456; 585/532
[58] Field of Search ...... 260/671 B, 671 G, 683.15 B; 585/24, 319, 456, 532

[56] References Cited

U.S. PATENT DOCUMENTS

| | | | |
|---|---|---|---|
| 2,518,529 | 8/1950 | de Casson | 260/671 G |
| 3,000,981 | 9/1961 | Favis | 260/671 B |
| 3,104,267 | 9/1963 | Antonsen et al. | 260/671 B |
| 3,410,925 | 11/1968 | Eby et al. | 260/671 G |

FOREIGN PATENT DOCUMENTS 1000560 2/1952 France.

*Primary Examiner*—C. Davis
*Attorney, Agent, or Firm*—Haseltine, Lake & Waters

[57] ABSTRACT

A process for preparing alkylbenzenes, according to which benzene is reacted with an olefin (or mixture of olefins) in the presence of a suitable catalyst, according to the Friedel-Crafts reaction. The reactant which is reacted with the benzene is the product of the autocondensation of an olefin or a mixture of olefins, having a number of carbon atoms of between 10 and 15, whereby a mixture of both light and heavy alkylbenzenes is obtained, the heavy alkylbenzenes being useful for lubricating compositions.

4 Claims, No Drawings

PROCESS FOR THE PREPARATION OF ALKYLBENZENES

This is a continuation of application Ser. No. 841,447, filed Oct. 12, 1977, which is a continuation-in-part of our U.S. patent application Ser. No. 694,228, filed June 9, 1976, both now abandoned.

The present invention relates to a process for synthetically preparing alkylbenzenes, more particularly to a process for the simultaneous production of a useful mixture of both light and heavy alkylbenzenes; the heavy alkylbenzenes are useful in the synthesis of additives for lubricating oils, as well as in the formulation of protecting agents, anti-rust and emulsifying agents, whereas light alkylbenzenes are useful for detergents.

In this field of the art it is known to use residual heavy alkylbenzenes resulting from the distillation either of linear or branched dodecylbenzene, or of the natural alkylaryls contained in the heavy fractions of crude oil distillation.

Heavy alkylbenzenes are also obtained by synthesis through the reaction of the benzene with heavy olefins purposely prepared from low molecular weight olefins, usually ethylene, propylene and butylene, homo- and hetero-oligomerized.

Although the products of natural origin show some drawbacks, such as the presence of not negligible amounts of undesirable components, or a variability of composition and, therefore, of properties, the synthesis starting from oligomers of low molecular weight olefins is affected by the disadvantages of rather low yields and of the necessary purification of the raw mixture which is reacted with benzene.

There has now been found, and constitutes the subject of the present invention, a process for the synthesis of alkylbenzenes which not only permits to obtain heavy alkylbenzenes with industrially advantageous yields and endowed with properties rendering them suitable for the aforesaid use in the lubrication field, but simultaneously leads to the formation of substantial amounts of relatively light alkylbenzenes, such as dodecylbenzene, the use of which in the field of synthetic detergents is well known.

To this end the process according to the present invention for producing alkylbenzenes, through a Friedel-Crafts synthesis between benzene and an olefin fraction, in the presence of a suitable catalyst, is characterized in that the olefin fraction consists of the product of the auto-condensation of an olefin or of a mixture of olefins, having a number of carbon atoms of between 10 and 15, said auto-condensation being carried out in the presence of a fresh catalyst.

According to the preferred embodiment of the process of the present invention, the olefin fraction undergoing the auto-condensation comprises n-olefins having an internal double bond, and the auto-condensation catalyst is selected amongst the catalysts of the Friedel-Crafts type, particularly aluminum halides, especially ALCl$_3$ and the residual catalyst of the auto-condensation step is used for the subsequent reaction with benzene without any separation or purification of the auto-condensation products.

Even if the process of the present invention generally contemplates the auto-condensation of olefins having a number of carbon atoms within the aforesaid interval, the n-olefins are preferred, preferably those having a number of carbon atoms of between 10 and 13. By n-olefins with internal double bond, the olefins are meant which, unlike the alpha-olefins (in which the double bond is localized in the 1-2 position) have the double bond statistically distributed along the entire molecule.

These n-olefins are obtained, for example, by the well-known Pacol-Olex process, by dehydrogenation of n-paraffins.

It has been found that the auto-condensation phase as carried out on these n-olefins, besides imparting to the heavy alkylbenzene the property of a raw material particularly suitable for use in the lubrication field, causes the conversion yields to be favorable both as regards the heavy alkylbenzenes and the light compounds, whereas the processes of the prior art were directed either to improve the yield and/or properties of the heavy compounds only or to the production of light compounds, without the possibility of satisfactorily obtaining both useful fractions.

According to the process of the invention the raw product containing unreacted olefins, oligomers of said olefins and other by-products, is reacted with benzene according to a normal Friedel-Crafts synthesis. The final product will contain light alkylbenzenes, heavy alkylbenzenes, as well as by-products of the paraffin type, the relative proportions being a function of conditions in which the condensation and alkylation reactions are carried out, but being anyhow, distinguished by the obtaining of two main fractions, i.e light and heavy alkylbenzenes, both of which are useful; furthermore the thus obtained heavy products are structurally different and show properties more suitable for use in lubrication.

A preferred embodiment of the process consists in carrying out the reaction with benzene immediately after the autocondensation, by taking advantage of the residual catalytic activity of the catalytic complex as originated by the condensation catalyst, thus affording a saving of catalyst and a relevant simplification of the process.

The condensation can be carried out under several conditions, comprising temperatures of between 20° and 200° C., preferably between 80° and 110° C., times of between 5 and 250 minutes, preferably between 50 and 150 minutes; and catalyst amounts of between 0.01% and 10%, preferably between 0.5% and 2% of the olefin. It is generally found that by increasing the times, the temperatures and catalyst percentages, the condensation yields are enhanced and therefore the yields are displaced towards the heavy alkylbenzenes, to the detriment of the light alkylbenzenes, the by-products being, however, also increased, and at the borderline also a decrease of the molecular weight taking place due to a degradation of the resulting products.

The optimum conditions are of course dependent on the catalyst which is used, as well as on the ratio of heavy alkylbenzene to light alkylbenzene which is considered as the most advantageous from the economical point of view.

As illustrated by the examples below, the process is expediently carried out in two steps: the autocondensation at 80°-105° C. for 90 to 100 min. using 1% AlCl$_3$ as catalyst and the reaction of the autocondensate with benzene (saturated with HCl) at 40° to 42° C. for 50-80 min. using an additional 2 to 2.75% AlCl$_3$ as catalyst.

The main advantage related to the present invention as regards the heavy fraction, resides in obtaining alkylbenzenes having high molecular weight, even higher than 500, and provided with side chains different from either those obtained starting from branched olefins, such as for instance the propylene tetramer, and those obtained from n-olefins, both of the alpha type and having an internal double bond. As a consequence, sulfonic derivatives are obtained, which are particularly oil soluble, having a very reduced tendency to foaming as well as a particularly high protecting capacity with respect to metal surfaces: all these properties are highly improved with respect to the normal alkylbenzenes prepared as above mentioned, even if the molecular weight is the same.

In the use of the said derivatives as additives for lubricating oils the obtained advantage is evident, and there has particularly been noted an increase of the detergent-dispersant properties of the alkali-earth metal sulfonates, as prepared from the subject alkylbenzenes, when evaluated both on the basis of the tendency to carry the carbon black in suspension, and on the basis of the cleaning degree of the pistons of the test engines.

The following Examples, not to be construed in a limiting sense, illustrate the invention with respect to a batch process, it being understood that the same process can be practiced in a continuous manner without difficulty.

EXAMPLE 1

A $C_{11}$–$C_{14}$ n-olefin cut, as obtained by dehydrogenation of the corresponding n-paraffins resulting from the PACOL-OLEX process, and containing:

n-undecene—19%
n-dodecene—30.2%
n-tridecene—25.3%
n-tetradecene—18%
light compounds—0.2%
heavy compounds—1%
isomers—3.7%
paraffins—0.5%
aromatics—1.4% was heated at 80° C. and then supplemented over 15 minutes, with 1% $AlCl_3$. The temperature was raised to 105° C. and the reaction mass was maintained at this temperature for 100 minutes. Then the reaction mass was cooled down to 40° C., and 2.75% $AlCl_3$ and an amount of benzene three times the weight of the starting olefin were added; the reaction mass was saturated with anhydrous HCl and reacted for 80 minutes at 40° C., then the final product, after separation from the heavy catalytic layer and washed with caustic solution, was distilled, the alkylated fraction having the following composition:

8.8%—light alkylate and paraffins;
13.6%—alkylate corresponding to a cut of linear dodecylbenzene useful for detergents;
77.6%—heavy alkylate with viscosity of 3.47° F. at 50° C. and bromine number of about 3.

EXAMPLE 2

A $C_{10}$–$C_{13}$ n-olefin cut, having the following distillation curve:

| IBP | 189° C. | (372.2° F.) |
|---|---|---|
| 5% | 193° C. | (379.4° F.) |
| 10% | 194° C. | (381.2° F.) |
| 20% | 196° C. | (384.8° F.) |
| 30% | 198° C. | (388.3° F.) |
| 40% | 200° C. | (392.0° F.) |
| 50% | 202° C. | (395.6° F.) |
| 60% | 204° C. | (399.2° F.) |
| 70% | 207° C. | (404.6° F.) |
| 80% | 211° C. | (411.8° F.) |
| 90% | 216° C. | (420.8° F.) |
| 95% | 221° C. | (429.8° F.) |
| E.P. | 230° C. | (446.0° F.) | was treated according to Example 1, except that the reaction temperature was 105° C. and the reaction time was 90 minutes.

A product was obtained having the following distillation curve:

| IBP | 189° C. | (372.2° F.) |
|---|---|---|
| 5% | 195° C. | (383.0° F.) |
| 10% | 199° C. | (390.2° F.) |
| 20% | 206° C. | (402.8° F.) |
| 30% | 214° C. | (417.2° F.) |
| 40% | 233° C. | (451.4° F.) |
| 50% | 319° C. | (606.2° F.) |
| 60% | 339° C. | (642.2° F.) |
| 70% | 349° C. | (660.2° F.) |
| 80% | 356° C. | (672.8° F.) |
| 90% | 361° C. | (681.8° F.) |

No data were obtainable above 90% due to decomposition.

From the preceding data it is readily appreciated that in the precondensate according to the present invention a boiling point higher than the end point (E.P.) of the starting cut is obtained only at the 40% level, which means that the fraction from 40 to 90% gives place to mono- and di-alkylated benzenes useful for the production of the oil soluble sulfonates, whereas the fraction below 40% gives place to light mono-alkylated benzenes, useful for detergents, and to di-alkylated benzenes corresponding to the non-condensed molecules.

The precondensate is then treated according to the Example 1, giving place to comparable results.

EXAMPLE 3

A $C_{11}$–$C_{14}$ n-olefin cut, like that used in Example 1, was supplemented at room temperature with 1% $AlCl_3$. The temperature was then raised to 105° C. and maintained for 100 minutes; the reaction mass was then cooled down to 40° C., and 2% $AlCl_3$ and an amount of benzene three times the weight of the starting olefin were added; the mass was saturated with anhydrous HCl and reacted for 50 minutes at 42° C.

The final product, after separation from the heavy catalytic layer and washing with caustic solution, was distilled, the alkylated fraction showing the following composition:

5.2%—light alkylated and paraffins;
29.0%—alkylate corresponding to a cut of linear dodecylbenzene useful for detergents;
65.8%—heavy alkylate.

The analysis of the light fraction, having a bromine number of 0.96, showed as the composition 33% of aromatics and 67% of paraffins; the alkylate of the dodecylbenzene type, having a bromine number of 0.09, showed an average molecular weight of 252, and the heavy alkylate, having a bromine number of 1.8, showed a viscosity of 4.37° F. at 50° C.

EXAMPLE 4

A $C_{11}$–$C_{14}$ n-olefin cut, like that used in the Example 1, was separated from a head fraction and a bottom fraction.

The center fraction, containing:
n-undecene—2.5%
n-dodecene—45.1%
n-tridecene—48.2%
n-tetradecene—4.2% was heated to 100° C. and slowly treated with 1% $AlCl_3$, and reacted at 100° C. for 100 minutes. Then the reaction mass was cooled down to 40° C., and 2.5% $AlCl_3$ and an amount of benzene three times the weight of the starting olefin were added; the mass was saturated with anhydrous HCl and reacted for 75 minutes at 42° C.

The final product, after separation from the heavy catalytic layer and washing with a caustic solution, was distilled and the alkylated fraction showed the following composition:
5.3%—light alkylate and paraffins
21.4%—alkylate corresponding to a dodecylbenzene cut useful for detergents
73.3%—heavy alkylate with a viscosity of 3.22° F. at 50° C. and bromine number of 2.6.

EXAMPLE 5

A n-olefin cut, like that used in the Example 3, was condensed under the same conditions, and similarly reacted with benzene, except that 2.75% $AlCl_3$ instead of 2.5% was used. The final product, after the same processing, showed the following composition:
5.2%—light alkylate and paraffins
18.7%—alkylate corresponding to a dodecylbenzene cut useful for detergents (bromine number: 0.02)
76.1%—heavy alkylate with a viscosity of 2.6° F. at 50° C., bromine number of 1.2 and average molecular weight of 410.

In connection with the process of the present invention, it is to be particularly pointed out that, due to the autocondensation step, the heavy alkylate does mainly comprise monoalkylbenzenes having an alkyl chain longer than that of the starting olefin, but also dialkylbenzenes are present having an alkyl chain corresponding to the starting olefin and useful as well for lubricating additives. In turn the light fraction is used as the raw material for the production of synthetic detergents, instead of being either disposed or recycled to the condensation or alkylation step.

What we claim is:

1. A method for producing heavy alkylbenzenes and linear dodecylbenzene comprising the steps of autocondensing a mixture of n-olefins with an internal double bond and having 11 to 14 carbon atoms in the presence of 1% by wt of $AlCl_3$ relative to the weight of said olefins at a temperature of from 80° C. to 105° C. and for a period of from 90 to 100 mins, allowing the autocondensation product to cool to 40° C., adding to said product from 2% to 2.75% by weight of $AlCl_3$ relative to the starting olefins, adding an amount of benzene equal to three times the weight of the starting olefins and saturating the resultant reaction mixture with gaseous hydrogen chloride, carrying out the reaction with benzene at about 40° C.–42° C. for a period of from 50 to 80 mins. to form a mixture of alkylbenzenes, washing the mixture of alkylbenzenes with a caustic alkali and subjecting the washed mixture to fractional distillation to separate the heavy alkylbenzenes and the linear dodecylbenzene.

2. The process of claim 1 carried out batch wise.
3. The process of claim 1 carried out continuously.
4. The product obtained by the process of claim 1.

* * * * *